(12) United States Patent
Roussev et al.

(10) Patent No.: US 11,703,500 B2
(45) Date of Patent: Jul. 18, 2023

(54) METHODS OF CHARACTERIZING ION-EXCHANGED CHEMICALLY STRENGTHENED GLASSES CONTAINING LITHIUM

(71) Applicant: CORNING INCORPORATED, Corning, NY (US)

(72) Inventors: Rostislav Vatchev Roussev, Painted Post, NY (US); Vitor Marino Schneider, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 17/873,495

(22) Filed: Jul. 26, 2022

(65) Prior Publication Data

US 2022/0373532 A1 Nov. 24, 2022

Related U.S. Application Data (60) Division of application No. 17/169,900, filed on Feb. 8, 2021, now Pat. No. 11,402,366, which is a division
(Continued)

(51) Int. Cl.
*G01N 33/38* (2006.01)
*C03C 21/00* (2006.01)
*G01L 1/00* (2006.01)

(52) U.S. Cl.
CPC ......... *G01N 33/386* (2013.01); *C03C 21/002* (2013.01); *G01L 1/00* (2013.01)

(58) Field of Classification Search
CPC ........ G01N 33/386; C03C 21/002; G01L 1/00
(Continued)

(56) References Cited

U.S. PATENT DOCUMENTS 8,415,013 B2 4/2013 Barefoot et al.
8,561,429 B2 10/2013 Allan et al.
(Continued)

FOREIGN PATENT DOCUMENTS

CN 100465119 C 3/2009
CN 103043900 A 4/2013
(Continued)

OTHER PUBLICATIONS

Abrams et al. "Fracture behavior of engineered stress profile soda lime silicate glass," Journal of Non-Crystalline Solids 321 (2003) pp. 10-19.
(Continued)

*Primary Examiner* — Md M Rahman
(74) *Attorney, Agent, or Firm* — Timothy Schaeberle (57) ABSTRACT

Methods of characterizing ion-exchanged chemically strengthened Li-containing glasses include: a) measuring a mode spectrum of the glass sample; b) using the mode spectrum, estimating a first contribution to the center tension associated with a spike region and estimating a second contribution to the center tension due to a deep region only, wherein the deep region is assumed to follow a power-law stress profile; and c) determining a total center tension by adding of the first and second contributions to the center tension. The methods can be used for quality control during manufacturing of glass samples by comparing the total center tension to a center tension specification that provides optimum strength and durability.

16 Claims, 7 Drawing Sheets

Related U.S. Application Data of application No. 16/247,078, filed on Jan. 14, 2019, now Pat. No. 10,914,721, which is a continuation of application No. 15/171,490, filed on Jun. 2, 2016, now Pat. No. 10,180,416.

(60) Provisional application No. 62/170,919, filed on Jun. 4, 2015.

(58) Field of Classification Search
 USPC .......................................................... 356/32
 See application file for complete search history.

(56) References Cited

U.S. PATENT DOCUMENTS

| | | |
|---|---|---|
| 8,957,374 B2 | 2/2015 | Liu et al. |
| 9,140,543 B1 | 9/2015 | Allan et al. |
| 9,499,431 B2 | 11/2016 | Barefoot et al. |
| 10,180,416 B2 | 1/2019 | Roussev et al. |
| 2012/0135195 A1 | 5/2012 | Glaesemann et al. |
| 2012/0194974 A1 | 8/2012 | Weber et al. |
| 2013/0045375 A1 | 2/2013 | Gross |
| 2013/0202868 A1 | 8/2013 | Barefoot et al. |
| 2013/0221053 A1 | 8/2013 | Zhang |
| 2013/0224492 A1 | 8/2013 | Bookbinder et al. |
| 2014/0065101 A1 | 3/2014 | Yokokawa |
| 2014/0102144 A1 | 4/2014 | Yamanaka et al. |
| 2014/0138420 A1 | 5/2014 | Peng et al. |
| 2014/0368808 A1 | 12/2014 | Roussev et al. |
| 2015/0030834 A1 | 1/2015 | Morey et al. |
| 2015/0066393 A1 | 3/2015 | Liu et al. |
| 2015/0147574 A1 | 5/2015 | Allan et al. |

FOREIGN PATENT DOCUMENTS

| | | |
|---|---|---|
| GB | 1253284 A | 11/1971 |
| JP | 53-136886 A | 11/1978 |
| JP | 54-120987 | 8/1979 |
| JP | 55-033675 | 3/1980 |
| JP | 2005-043165 A | 2/2005 |
| JP | 2015-511573 A | 4/2015 |
| JP | 2016-142600 A | 8/2016 |
| WO | 2015/077179 A1 | 5/2015 |

OTHER PUBLICATIONS

Chinese Patent Application No. 201680032616.4; English Translation of the First Office Action dated Dec. 3, 2019; China Patent Office; 7 pgs.

International Preliminary Report on Patentability of the International Searching Authority; PCT/US16/35449; dated Dec. 14, 2017; 7 pages; European Patent Office.

International Search Report and Written Opinion PCT/US2016/035449 dated Sep. 9, 2016.

Japanese Patent Application No. 2020-073971 Office Action dated Mar. 2, 2021, 4 pages (2 pages of English Translation and 2 pages of Original Document); Japanese Patent Office.

Chinese Patent Application No. 202011567332.X, Office Action dated Nov. 3, 2022, 5 pages (English Translation only), Chinese Patent Office.

METHODS OF CHARACTERIZING ION-EXCHANGED CHEMICALLY STRENGTHENED GLASSES CONTAINING LITHIUM

CROSS-REFERENCE TO RELATED APPLICATIONS

This Application is a divisional of U.S. patent application Ser. No. 17/169,900 filed on Feb. 8, 2021, which is a divisional of U.S. patent application Ser. No. 16/247,078 filed on Jan. 14, 2019, which is a continuation of U.S. patent application Ser. No. 15/171,490 filed on Jun. 2, 2016, which claims the benefit of priority under 35 USC § 119(e) of U.S. Provisional Patent Application No. 62/170,919, filed on Jun. 4, 2015, and which is incorporated by reference herein.

FIELD

The present disclosure relates to chemically strengthened glass, and in particular relates to methods of characterizing ion-exchanged chemically glasses containing lithium.

BACKGROUND

Chemically strengthened glasses are glasses that have undergone a chemical modification to improve at least one strength-related characteristic, such as hardness, resistance to fracture, etc. Chemically strengthened glasses have found particular use as cover glasses for display-based electronic devices, especially hand-held devices such as smart phones and tablets.

In one method, the chemical strengthening is achieved by an ion-exchange process whereby ions in the glass matrix are replaced by externally introduced ions, e.g., from a molten bath. The strengthening generally occurs when the replacement ions are larger than the native ions (e.g., Na+ ions replaced by K+ ions). The ion-exchange process gives rise to a refractive index profile that extends from the glass surface into the glass matrix. The refractive index profile has a depth-of-layer or DOL that defines a size, thickness or "deepness" of the ion-diffusion layer as measured relative to the glass surface. The refractive index profile also defines a number of stress-related characteristics, including stress profile, surface stress, center tension, birefringence, etc. The refractive index profile defines an optical waveguide when the profile meets certain criteria.

Recently, chemically strengthened glasses with a very large DOL (and more particularly, a large depth of compression) have been shown to have superior resistance to fracture upon face drop on a hard rough surface. Glasses that contain lithium ("Li-containing glasses") can allow for fast ion exchange (e.g., Li+ exchange with Na+ or K+) to obtain a large DOL. Substantially power law (e.g., substantially parabolic) stress profiles are easily obtained in Li-containing glasses, where the ion-exchange concentration profile of Na+ connects in the central plane of the substrate, shrinking the traditional central zone of the depth-invariant center tension to zero or negligible thickness. The associated stress profiles have a predictable and large depth of compression, e.g., on the order of 20% of the sample thickness, and this depth of compression is quite robust with respect to variations in the fabrication conditions.

An example power law stress profile of particular commercial importance is a near-parabolic (substantially parabolic) profile for the deep region that joins to a "spike" portion near the surface. This spike portion ("spike") is particularly helpful in preventing fracture when glass is subjected to force on its edge (e.g., a dropped smart phone) or when the glass experiences significant bending. The spike can be achieved in Li-containing glasses by ion exchange in a bath containing $KNO_3$. It is often preferred that the spike be obtained in a bath having a mixture of $KNO_3$ and $NaNO_3$ so that Na+ ions are also exchanged. The Na+ ions diffuse faster than K+ ions and thus diffuse at least an order of magnitude deeper than the K+ ions. Consequently, the deeper portion (region) of the profile is formed mainly by Na+ ions and the shallow portion of the profile is formed mainly by K+ ions.

In order for chemically strengthened Li-containing glasses to be commercially viable as cover glasses and for other applications, their quality during manufacturing must be controlled to certain specifications. This quality control depends in large part on the ability to control the ion-exchange process during manufacturing, which requires the ability to quickly and non-destructively measure the refractive index (or stress) profiles.

Unfortunately, the quality control for glasses with spike stress profiles is wanting due to the inability to adequately characterize the profiles in a non-destructive manner. This inability has made manufacturing of chemically strengthened Li-containing glasses difficult and has slowed the adoption of chemically strengthened Li-containing glasses in the market.

SUMMARY

An aspect of the disclosure is directed to methods of characterizing chemically strengthened Li-containing glasses having a surface stress spike, such as produced by an ion-exchange process whereby Li+ is exchanged with K+ and Na+ ions (i.e., Li+⇔K+, Na+). The methods result in a measurement of the surface compression and the depth of the spike, and its contribution to the center tension, as well as the compression at the bottom of the spike, and the total center tension.

The method is preferably carried out to obtain a commercially important stress profile. An example of such a profile follows a power law (e.g., substantially parabolic) in most of the interior ("deep region") of the substrate other than the spike region ("spike") adjacent the substrate surface. The spike is generally formed by the slower diffusion (and thus shallower) K+ ions while the power-law portion is formed by the faster (and thus deeper) diffusing Na+ ions. The method allows for confirmation that the profile has reached the power-law, e.g., has a self-consistency check. The method can also include performing quality control of the glass samples being process. Such quality control is important for a commercially viable manufacturing process.

An aspect of the method involves measuring the mode lines or fringe spectrum of the K+ spike layer of the glass sample using a prism-coupling system to calculate surface stress (CS), depth of the spike (DOS), and the center tension (CT) contribution of the spike. In addition, a shift of an intensity transition corresponding to index at the depth of the bottom of the spike is measured, providing an estimate of the stress at the bottom of the spike. The depth of the spike ($DOS_{sp}$) and the depth of layer (DOL) is used to verify that the rest of the profile is in the power-law regime. Then the total CT is estimated assuming that the profile is follows a power law, taking into account the CT contribution of the spike. If the profile is expected to deviate moderately from a power law, the expected deviation can be accounted for by an adjustment factor in the target CT. If necessary, the depth of compression (DOC) is also estimated, taking into account the reduction of DOC resulting from the spike, relative to the DOC of a power-law profile.

In another aspect of the method, relationship is defined between the measurement wavelength and the target properties of the Na+-enriched deeper portion of the profile to help ensure a precise measurement of the compression at the bottom of the spike, and the most precise estimate of the CT and frangibility.

In another aspect of the method, a prism-coupling measurement of the mode spectrum is combined with a measurement of the weight gain, or measurements of the sample thickness and the sample weight, to estimate the amount of Na+ diffused in the sample.

Advantages of the methods disclosed herein include that they are non-destructive and high-throughput, and can provide a measurement of critical parameters of the stress profile with high precision. These parameters include the compressive stress CS, depth of spike DOS, depth of layer DOL, center tension CT and frangibility status, which is based on the center tension CT.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

In the discussion below, the term "power law" refers to a function that in an example follows the general form $f(x) = ax + bx^2 + cx^3 + dx^4 \ldots$, where a, b, c and d are coefficients.

Figure 1A:
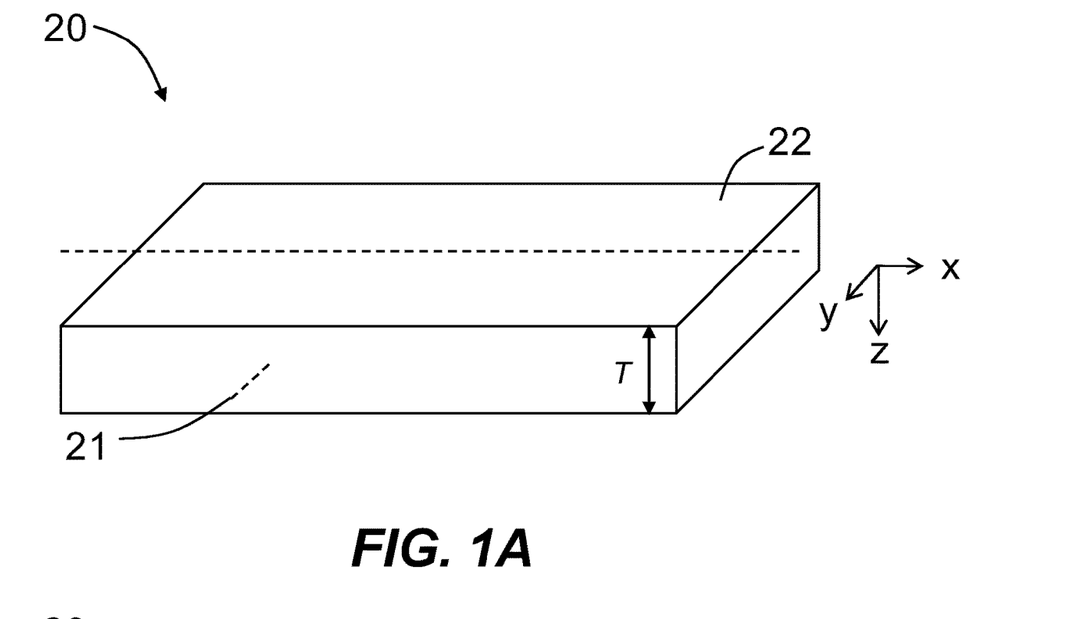
FIG. 1A is an elevated view of an example DIOX glass substrate in the form of a planar substrate.
Figure 1B:
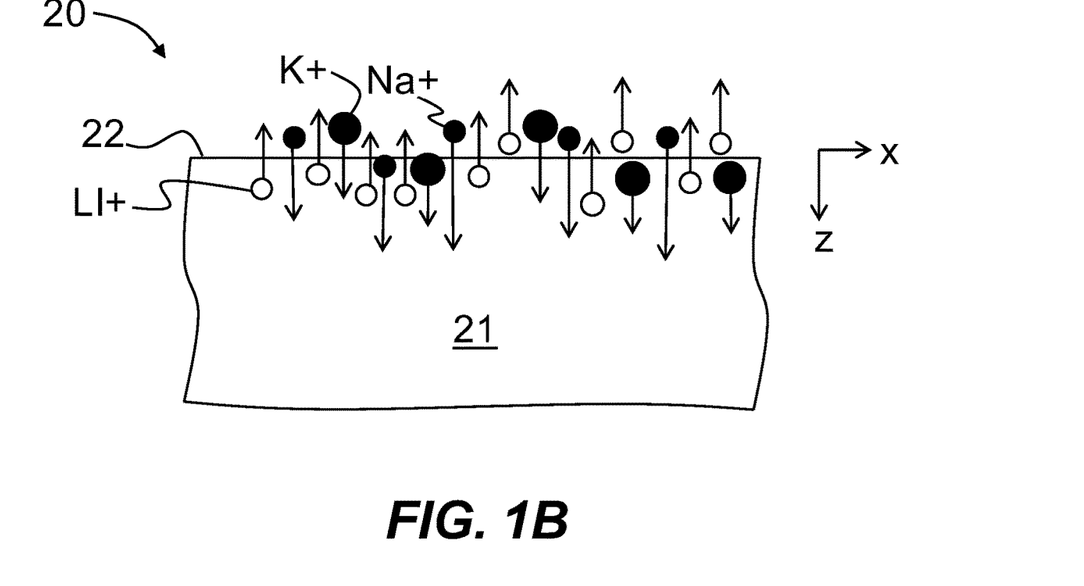
FIG. 1B is a close-up cross-sectional view of the DIOX substrate of FIG. 1A as taken in the x-z plane and that illustrates the double ion-exchange process that takes place across the substrate surface and into the body of the substrate.

FIG. 1A is an elevated view an example glass substrate in the form of a planar ion-exchanged substrate 20 that has a body 21 and a (top) surface 22, wherein the body has a base (bulk) refractive index $n_s$, a surface refractive index $n_0$ and a thickness T in the z-direction. FIG. 1B is a close-up cross-sectional view of ion-exchanged substrate 20 as taken in the y-z plane and illustrates an example double ion-exchange (DIOX) process that takes place across surface 22 and into body 21 in the z-direction.

In the DIOX process discussed in connection the method disclosed herein, two different types of ions Na+ and K+ replace another different ion Li+ that is part of the glass body 21. The Na+ and K+ ions can be introduced into the glass body 21 either sequentially or concurrently using known ion-exchange techniques. As noted above, the Na+ ions diffuse faster than the K+ ions and thus go deeper into the glass body 21. This has an effect on the resulting refractive index profile and stress profile, as discussed below.

Figure 1C:
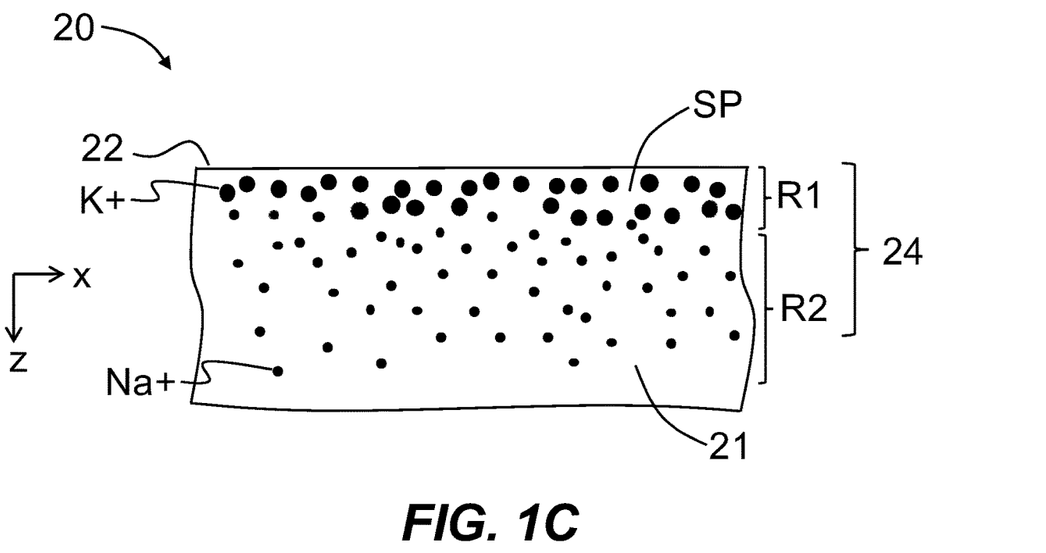
FIG. 1C schematically illustrates the result of the DIOX process that forms the DIOX substrate.
Figure 2:
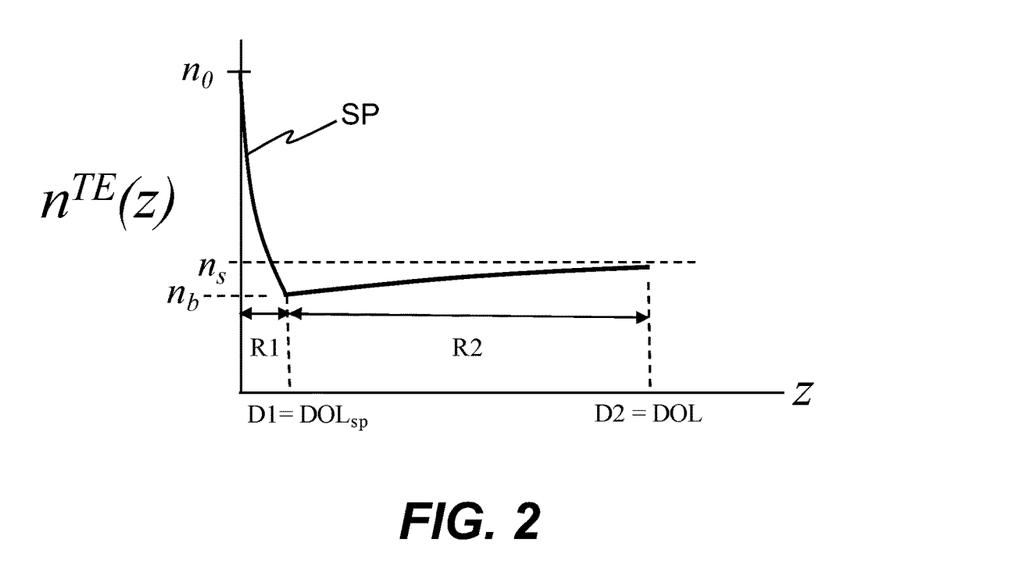
FIG. 2 is a representation of an example refractive index profile n(z) for the DIOX substrate illustrated in FIG. 1C.

FIG. 1C is a schematic diagram of the resulting DIOX process, and FIG. 2 is a representation of an example refractive index profile n(z) for substrate 20 having undergone the DIOX process and having a refractive index profile such as illustrated in FIG. 1C. The corresponding stress profile can be represented by σ(z). The refractive index profile n(z) includes a first "spike" region R1 associated with the shallower ion-exchange (K+ ions) and that has a depth D1 into body 21 that defines a "depth-of-layer for the spike" denoted hereinafter as $DOL_{sp}$. The refractive index profile n(z) also includes a second region R2 associated with the deeper ion-exchange (Na+ ions) and that has a depth D2 that defines the depth-of-layer (DOL).

The deeper second region R2 may be produced in practice prior to the shallower region. The region R1 is adjacent substrate surface 22 and is relatively steep and shallow, whereas region R2 is less steep and extends relatively deep into the substrate to the aforementioned depth D2. In an example, region R1 has a maximum refractive index $n_0$ at substrate surface 22 and steeply tapers off to an intermediate index $n_i$, while region R2 tapers more gradually from the intermediate index down to the substrate (bulk) refractive index $n_s$. The portion of the refractive index profile n(z) for region R1 represents a "spike" in the refractive index having a depth DOS.

Figure 3:
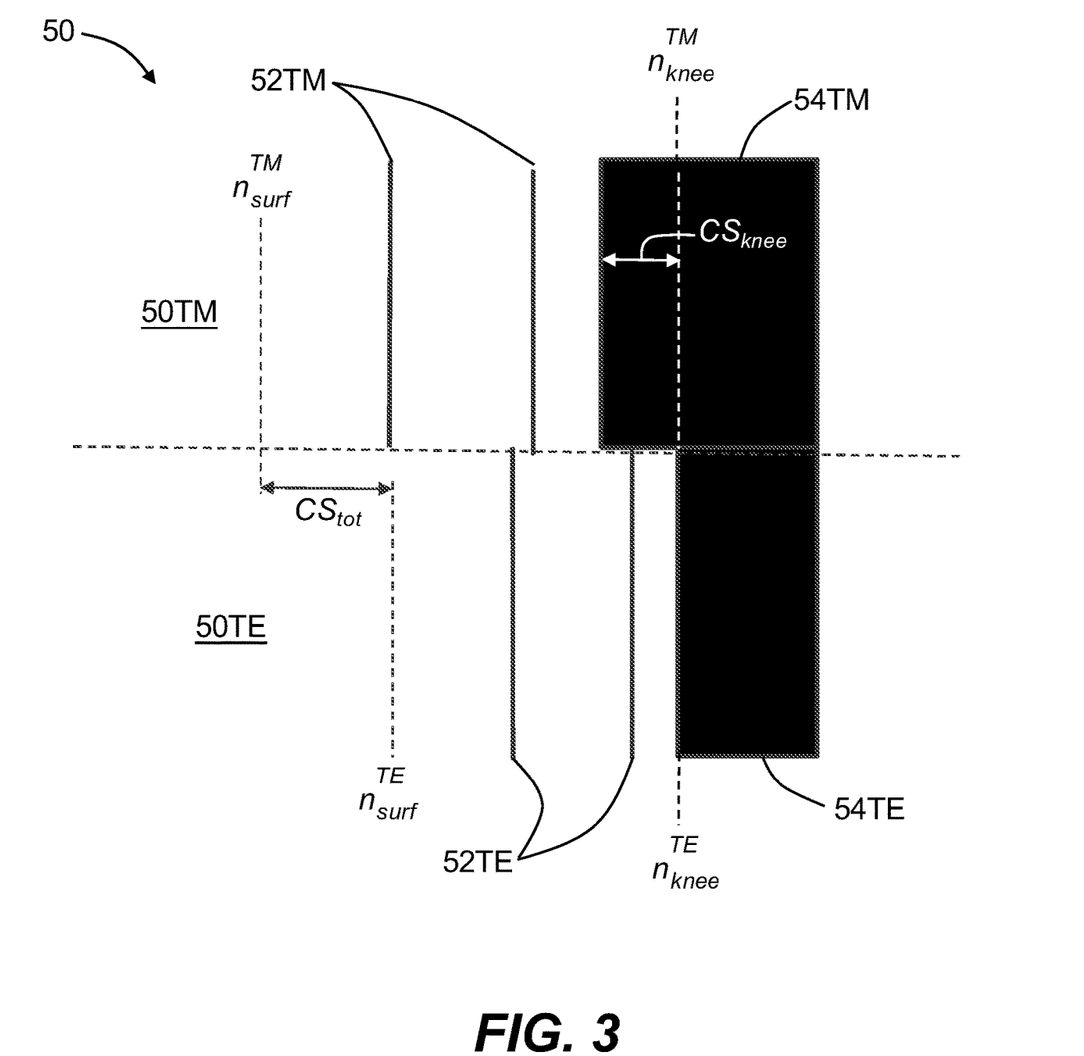
FIG. 3 is a schematic representation of an example measured mode spectrum of a Li-containing glass formed by an ion-exchange process using a mixture of $NaNO_3$ and $KNO_3$, with the mode spectrum including TM (top) and TE spectra (bottom), and also showing profile measurement parameters as explained below.

FIG. 3 is schematic representation of an example measured mode spectrum 50 of a Li-containing glass formed by an ion-exchange process using a mixture of $NaNO_3$ and $KNO_3$, with the mode spectrum including TM and TE spectra 50TM and 50TE (upper and lower portions, respectively) with respective mode lines 52TM and 52TE. The glass type is 196HLS with a fictive temperature of 638° C. The glass was subjected to a Li+⇔K+, Na+ ion-exchange process by placing the glass sample in a bath having 60 wt % $KNO_3$ and 40 wt % $NaNO_3$ at 390° C. for 3 hours.

As is known in the art, the fringes or mode lines 52TM and 52TE in the mode spectrum can be used to calculate surface compression or "compressive stress" CS and depth of layer DOL associated with an ion-exchange layer that forms an optical waveguide. In the present example, the mode spectrum 50 was obtained using a commercially available prism-coupling system, namely the FSM6000L surface stress meter ("FSM system"), available from Luceo Co., Ltd. of Tokyo, Japan. Example prism-coupling systems suitable for use for carrying out the methods disclosed herein are also described in U.S. Patent Applications No. 2014/0368808 and 2015/0066393, which are incorporated by reference herein.

The measured values of CS and DOL were 575 MPa and 4.5 microns, respectively. These are the parameters of the K+ enriched layer or spike region R1 adjacent sample surface 22. The auxiliary vertical dashed lines on the left hand side of the spectrum were added to FIG. 3 and show positions in the spectrum in which the conventional FSM system assigns to correspond to the surface index, one for TM, and one for TE. The difference in these positions is proportional to the surface stress or compressive stress CS, which is denoted "$CS_{tot}$" in FIG. 3 to indicate the total or maximum amount of surface stress. These positions are also used in the calculation of DOL.

The present inventors have recognized that in the mode spectrum 50 for a chemically strengthened Li-containing glass having undergone a Li+⇔K+, Na+ ion exchange, the position of transition from the bright to the dark portion of the spectrum, observed after the last fringe 52 in the spectrum that corresponds to the highest-order guided mode, is shifted in the TE spectrum 50TE as compared to the TM spectrum 50TM. This shift is proportional to the compressive stress CS at the depth at which the K+ concentration in spike region R1 decreases approximately to the constant-level concentration originally in the substrate (e.g., the spatially constant concentration in the glass matrix that makes up substrate body 21). The effective index of the transition corresponds to the effective index that occurs at the depth of a characteristic "knee" or transition in the stress profile, and the shift of the transition between the TE and TM spectra is proportional to the compressive stress at the depth of the knee (i.e., at the depth of the spike $D1=DOL_{sp}$).

The measurements of the mode spectrum 50 provided by the K+ penetration resulting from ion exchange, along with the shift in the intensity transition (e.g., transition from total internal reflection (TIR) to partial reflection as defined by the critical reflection angle in the prism-coupler system used), can be combined and used for effective quality control of a family of stress profiles that provide superior resistance to fracture. The profiles of this family are similar in shape to a power-law profile (region R2) with a spike (region R1).

The spike is small in thickness when compared to the substrate thickness T. For example, the spike may be 10 microns deep (i.e., $DOL_{sp}=10$ microns), while the substrate may be T=800 microns thick. The spike may have a shape similar to a complementary error function (erfc) shape, but may also be similar to a linear depth distribution, Gaussian depth distribution, or another distribution. The main features of the spike are that it is a relatively shallow distribution and it provides substantial increase of surface compression over the level of compression at the bottom of the spike as defined by $DOL_{sp}$.

Figure 4:
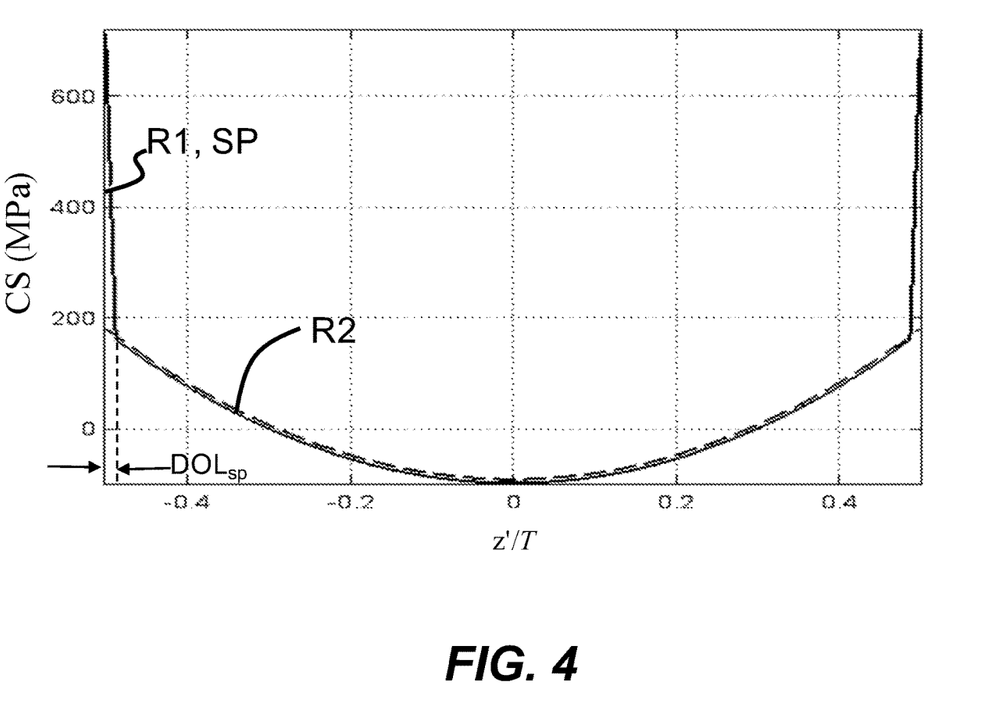
FIG. 4 is a plot of the compressive stress CS_(MPa) versus a normalized position coordinate z/T, showing the model stress profile (solid line) for a sample chemically strengthened Li-containing glass that has undergone a K+ and Na+ ion exchange, wherein the dashed line represents the model profile for Na+ diffusion only, noting that the model profile has ion exchange taking place at two surfaces that respectively reside at z/T=−0.5 and +0.5.

FIG. 4 is a plot of the compressive stress CS (MPa) versus a normalized position coordinate z/T, showing the model stress profile (solid) for a sample chemically strengthened Li-containing glass that has undergone a K+ and Na+ ion exchange, wherein the dashed line represents the model profile for Na+ diffusion only (note that the model profile has ion exchange taking place at two surfaces that respectively reside at z/T=−0.5 and +0.5). The profile has a parabolic deep portion or region R2 and a surface spike portion or region (or just "spike") R1.

In the present disclosure, the assumed convention is that compressive stress CS is positive and tensile stress is negative. The model profile of FIG. 4 has a linear spike R1 added on top of a deep quadratic profile R2. Another feature of the spike is also recognized from FIG. 4, namely that the typical slope of the stress distribution in the spike R1 is significantly higher than the typical slope in the deep portion R2 of the profile, which is assumed to follow a power law, and can be approximated as parabolic for the purposes of making measurements that can be used for quality control.

The profiles that are adequately approximated as parabolic for the purposes of the quality-control measurement method of the present disclosure have a distribution of Na+ ions such that over the range of depths from the bottom of the spike to the center of the thickness (i.e., from $z=DOL_{sp}$ to T/2), the minimum Na+ concentration is at the center of the thickness (i.e., at x/L=0 in FIG. 4), and the increase in concentration at the bottom of the spike relative to the minimum concentration at the center of thickness is approximately 3 to 7 times higher than the increase in concentration at a depth equal to one quarter of the thickness, i.e., T/4. In some cases, the increase in Na+ concentration anywhere within the depth of the spike relative to the concentration in the center of the substrate may be 3 to 7 times higher than the increase in Na+ concentration (relative to the center concentration) at depth equal to one quarter of the thickness.

In one embodiment of the method, the compressive stress $CS_{knee}$ and the depth of the spike are measured using a conventional prism-coupling measurement, e.g., using the aforementioned FSM system. Then a CT contribution of the spike $CT_{SP}$ is calculated using the equation:

$$CT_{sp} = \frac{CS_{SP} \times DOL_{sp}}{T - DOL_{sp}}$$

where T is the aforementioned sample thickness. The contribution to center tension of the Na+ profile $CT_{par}$, which is assumed parabolic, is calculated as:

$$CT_{par} \approx |0.5\sigma_{knee}|$$

where $\sigma_{knee}$ is the tensile stress at the knee of the profile, e.g., at the bottom of the spike and is given by:

$$\sigma_{knee} = \frac{(n_{crit}^{TE} - n_{crit}^{TM})}{SOC}$$

where $n_{crit}^{TE}$ and $n_{crit}^{TM}$ are the effective indices of the critical-angle intensity transitions as illustrated on FIG. 1. SOC is the stress-optic coefficient. Note that since tensile stress is the opposite (or negative) of compressive stress, $-\sigma_{knee}=CS_{knee}$, so that the magnitude of these two quantities is the same.

As illustrated by the dashed line of FIG. 2, the assumed power-law profile may be considered as an auxiliary profile that does not include the spike and that extends the profile shape all the way to the surface of the sample. This auxiliary profile is force-balanced, having its own CT, and is hence shifted vertically from the power-law portion of the model spiked power-law profile. The auxiliary profile has a compression depth is given by $$DOC_{par} = 0.5T\left(1 - \frac{1}{\sqrt{3}}\right) \approx 0.2113T$$

The total center tension equals the sum of the contributions of the spike and of the power-law portion:

$$CT_{tot} = CT_{par} + CT_{sp}.$$

The depth of compression DOC of the spiked power-law profile can be calculated by using the expression:

$$DOC = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx$$

$$DOC_{par}\left(1 - \frac{CT_{sp}}{2CT_{par}(\sqrt{3}-1)}\right) \approx DOC_{par} - \frac{0.5T}{\sqrt{3}} \frac{CT_{sp}}{2CT_{par}}$$

The approximate expressions at the end of the above equation are valid when the CT contribution of the spike is significantly smaller than the CT contribution of the auxiliary power-law profile.

In summary, the above-described method includes: 1) measuring the mode spectrum due to the spike and estimating a contribution of the spike to the center tension; 2) using the mode spectrum, measuring the shift of the critical angle; 3) estimating a compression at the knee, which is proportional to the contributions of the substantially power-law profile and of the spike.

In addition, a compression depth DOC of the profile may be estimated by using an exact formula for the model profile, or an approximate formula that gives the DOC as the DOC of an auxiliary power-law profile (e.g., parabolic or nearly parabolic) less a small DOC reduction due to the spike.

Furthermore, in one example embodiment, the depth of spike $DOL_{sp}$ is used to verify that the deep portion of the profile (region R2) is in a regime well represented by the power-law profile shape. In particular, as the $DOL_{sp}$ of the spike increases, the penetration of Na+ increases approximately in proportion to the $DOL_{sp}$ of the spike. Hence, for a glass where simultaneous in-diffusion of K+ and Na+ is used, a minimum $DOL_{sp}$ can be set for any particular glass thickness, above which the deep portion of the profile can be considered to follow a power law. In another example, an upper limit of the $DOL_{sp}$ may also be imposed to exclude physical profiles that start to deviate substantially from the parabolic model as a result of stress relaxation, which may become prominent at very long ion exchange times at high temperature.

The above-described method is a somewhat simplified version of a more precise method. The simplification incurs only a minor error when the CT contribution of the spike is much smaller than the CT contribution of the auxiliary power-law profile. The CT contribution of the spike shifts the power-law portion vertically by the amount CT, relative to the auxiliary power-law profile. As a result, the compression at the knee of the model spiked profile is actually smaller than the compression of the auxiliary profile at the knee depth by the amount $CT_{sp}$.

Furthermore, there is a minor change in compression of the auxiliary power-law profile between the surface and the depth of the knee, and, for a force-balanced power-law profile the CT is actually equal to half of the surface compression.

The following steps represent an example of a more precise method for determining the parameters of the model spiked power-law profile from the prism-coupling measurements:

a) Calculate preliminary $$CT_{sp}^{(0)} = \frac{(CS_{tot} - CS_{knee}) \times DOL_{sp}}{T - DOL_{sp}}$$

b) Calculate preliminary $$CS_{par}^{(0)} = \frac{CS_{knee} + CT_{sp}^{(0)}}{1 - 6\frac{DOL_{sp}}{T} + 6\frac{DOL_{sp}^2}{T^2}}$$

c) (Optional alternative to steps 4, 5, and 6) Calculate preliminary $$CT_{par}^{(0)} = 0.5CS_{par}^{(0)} = 0.5\frac{CS_{knee} + CT_{sp}^{(0)}}{1 - 6\frac{DOL_{sp}}{T} + 6\frac{DOL_{sp}^2}{T^2}} \text{ and } CT_{tot}^{(0)} = CT_{par}^{(0)} + CT_{sp}^{(0)}$$

d) Calculate more precise $$CT_{sp}^{(1)} = \frac{(CS_{tot} \cdot CS_{par}^{(0)}) \times DOL_{sp}}{T \cdot DOL_{sp}}$$

e) Calculate more precise $$CS_{par}^{(1)} = \frac{CS_{knee} + CT_{sp}^{(1)}}{1 - 6\frac{DOL_{sp}}{T} + 6\frac{DOL_{sp}^2}{T^2}},$$

$$\text{and } CT_{par}^{(1)} = 0.5CS_{par}^{(1)} = 0.5\frac{CS_{knee} + CT_{sp}^{(1)}}{1 - 6\frac{DOL_{sp}}{T} + 6\frac{DOL_{sp}^2}{T^2}}$$

f) Calculate more precise $CT_{tot}^{(1)} = CT_{par}^{(1)} + CT_{sp}^{(1)}$ g) (Optional)—Can continue iteration, finding more and more precise values for $CT_{sp}$ and $CS_{par}$, until desired level of convergence or precision. More than one iteration would rarely be of use, since actual profiles are unlikely to be precisely power law and have a precisely linear spike. More than one iteration may be useful in relatively thin substrates in which the depth of the spike may represent more than about 3% of the substrate thickness.

h) (Optional) Determine depth of compression DOC of the profile, for example using one of the forms of the equation:

$$DOC = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx$$

$$DOC_{par}\left(1 - \frac{CT_{sp}}{2CT_{par}(\sqrt{3} - 1)}\right) \approx DOC_{par} - \frac{0.5T}{\sqrt{3}} \frac{CT_{sp}}{2CT_{par}}$$

In the case where one is working directly with the DOL as measured by conventional means and not the real depth of layer or position of the spike, a range of approximations may be needed, some of which are empirical in nature.

In many cases, the power-law profile can be estimated as parabolic or substantially parabolic, i.e., to the power 2. In other cases, substantially nonlinear diffusion may cause the shape of the deep portion of the stress profile to be best represented by a relatively high power-law profile, e.g., to the power 3, i.e., cubic, or even higher. The methods that employ profiles greater than parabolic can be used to improve the accuracy with which the quality-control model represents the actual stress profile, and in this way to increase the range of ion exchange conditions over which the quality control method works effectively for the particular glass of interest.

For example, for a parabolic profile the ratio of CS to CT by absolute value is 2. Similarly, for a cubic profile the corresponding ratio is 3, and for a quartic profile it is 4. A force-balanced profile representation using the power of 3/2 has a CS to CT ratio of 1.8. Note that for power-function profile where the power is not an even number, the profile is constructed as the absolute value of the power function. In the mentioned examples, the depth of compression for the non-spiked auxiliary profile is about 0.23T for the profile with power 3/2, 0.21T for the power-law profile, 0.185T for the cubic profile, and 0.165T for the quartic profile.

Once a model-profile shape is found to represent the relatively stable shape of the center-connected concentration and stress profile, the corresponding ratio of CS to CT and DOC estimate can be used for the auxiliary profile in the application of the method of the present invention for quality control.

Thus, in a more generic embodiment of the invention, the auxiliary deep portion of the spiked profile may be represented with a symmetric absolute value of a power function of the distance from the center, and an associated ratio of CS to CT of a force-balanced profile having the shape of the model function is used to estimate the CT from the measured compression at the knee or estimated compression at the surface. If the depth of compression is also sought, the depth of compression of the model profile may be used as an approximate reference, or the depth of compression of the full force-balanced model profile may be calculated as was done for the example spiked power-law profile. In an example, the ratio CS to CT ranges from about 1.8 to about 4, while the DOC for the auxiliary model profile ranges from about 0.16T to about 0.23T.

Figure 5:
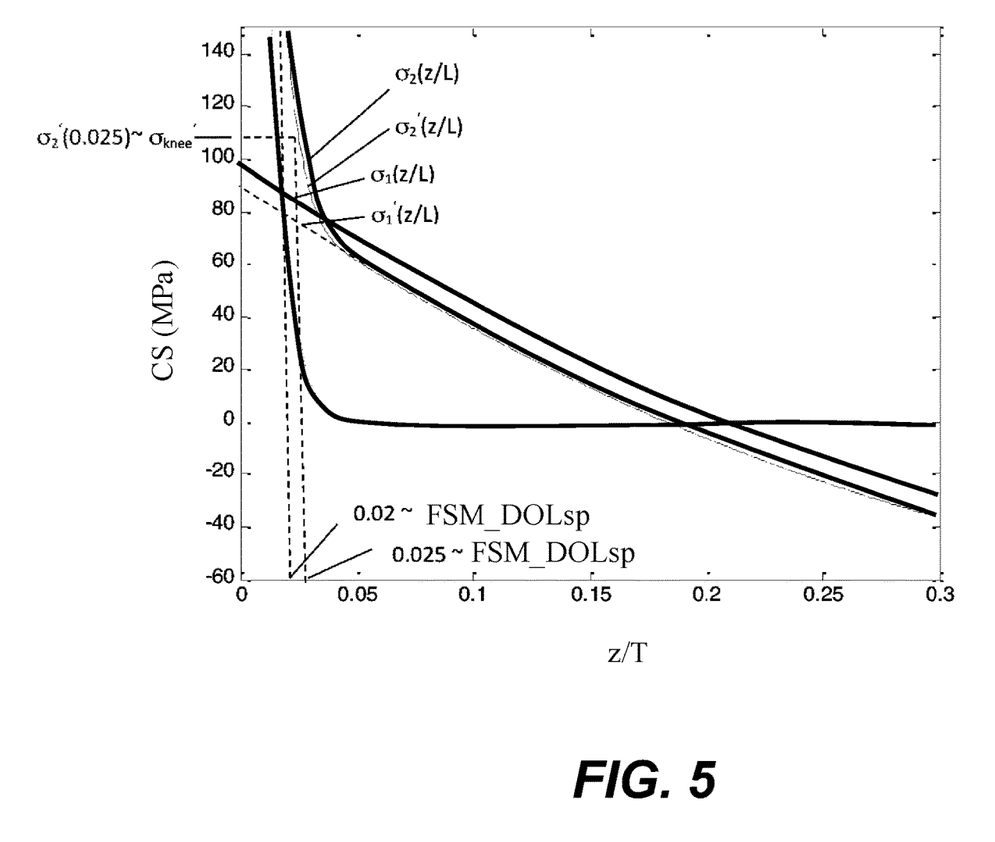
FIG. 5 is a plot of the stress (MPa) versus a normalized position coordinate z/T showing separate plots for the spike portion, the long diffused power-law portion and the spike plus power-law portion of the stress profile.

FIG. 5 is a plot of the stress (MPa) versus a normalized position coordinate x/L and shows separate plots for the spike portion, the long diffused power-law portion and the spike plus power-law portion of the stress profile. Another embodiment uses the parabolic auxiliary profile as illustrated in FIG. 4 and the following representation for the force-balanced power-law profile (the solid line):

$$\sigma_1\left(\frac{z}{L}\right) = \sigma_1(0)\left[-\frac{1}{2} + 6\left(\frac{z}{L} - 0.5\right)^2\right] \quad (1)$$

A conventional measurement (e.g., using the aforementioned FSM system) is used to measure "FSM_DOL" of the spike as approximately the diffusion depth given by $2\sqrt{D \cdot \tau}$ where D is the diffusion coefficient and $\tau$ is the time of diffusion. Then, using the fact above where $\sim 1.25 \times$ FSM_DOL leads to most of the area of the spike to be included, one can get an approximate equation for the CT due to the spike contribution, namely $$CT_{spike} = \frac{(\sigma'_2(0) - \sigma'_2(1.25 \times FSM\_DOL)) \times 1.25 \times FSM\_DOL}{T - 1.25 \times FSM\_DOL} \quad (2)$$

The point $\sigma_2 \cdot (1.25 \times FSM\_DOL)$ although not equal to is acceptably close to the CS between the transition between guided modes and continuum in the spiked lithium glass samples. This point is called the $CS_{knee}$ and is shown in FIG. 3 as a reasonable approximation. It is also reasonable to approximate the stress and the offset due to the contribution of the $CT_{spike}$ deeper inside the glass.

Since the power-law profile will be slowly varying as compared to the spike portion of the profile, it can be assumed that the stress at $\sim(2-3)\times FSM\_DOL$ in the power-law region would not feel the presence of the spike. It therefore follows that:

$$\sigma_1\left(\frac{z}{L}\right) \cong \sigma'_1\left(\frac{z}{L}\right) + CT_{spike} \quad (3)$$

and, $$\sigma_1\left(\frac{3 \times FSM\_DOL}{L}\right) \cong \sigma'_1\left(\frac{3 \times FSM\_DOL}{L}\right) + CT_{spike} \quad (4)$$

Using the parabolic power-law equation in (1), one establish the following relationships:

$$\sigma_1\left(\frac{3 \times FSM\_DOL}{L}\right) = \quad (5)$$

$$\sigma_1(0)\left[-\frac{1}{2} + 6\left(\frac{3 \times FSM\_DOL}{L} - 0.5\right)^2\right] \cong \sigma'_1\left(\frac{3 \times FSM\_DOL}{L}\right) + CT_{spike}$$

and $$\sigma_1(0) \cong \frac{\sigma'_1\left(\frac{3 \times FSM\_DOL}{L}\right) + CT_{spike}}{\left[-\frac{1}{2} + 6\left(\frac{3 \times FSM\_DOL}{L} - 0.5\right)^2\right]} \quad (6)$$

Numerically it can be demonstrated that if one uses a factor 2 instead of 3, the results are almost the same, in some cases varying by just 1%-2% of $\sigma_1(0)$. Therefore, if one can find the approximated value of $$\sigma'_1\left(\frac{3 \times FSM\_DOL}{L}\right) \text{ or } \sigma'_1\left(\frac{2 \times FSM\_DOL}{L}\right)$$

in the FSM, one can use equation (6) to compute the original stress of the first stress parabola within this range of error.

In practice one can measure approximately $$\sim \sigma'_1\left(\frac{3 \times \text{FSM\_DOL}}{L}\right) \text{ to } \sim \sigma'_1\left(\frac{2 \times \text{FSM\_DOL}}{L}\right) \quad 5$$

by examining the stress generated at the transition between guided modes and continuum in the spike on Li-glass samples. This point where approximately $$\sim \sigma'_1\left(\frac{3 \times \text{FSM\_DOL}}{L}\right) \text{ to } \sim \sigma'_1\left(\frac{2 \times \text{FSM\_DOL}}{L}\right)$$

can be used as the point $CS_{knee}$ as shown in FIG. 3 as a reasonable approximation that can be measured by computing the distance between these lines (fringes) in TM and TE spectra and their refractive index. In light of the stress optical coefficient (SOC) of the material the division of the index difference at this point per the SOC would lead to the $CS_{knee}$ stress values.

This in addition to the FSM_DOL and the $CS \sim \sigma_2'(0)$ given by the FSM for the spike. Therefore $CT_{parabola} = CT_{par} \sim \sigma_1(0)/2$, and $CT_{spike}$ is given in (2) as (repeated for convenience)

$$CT_{spike} = \frac{(\sigma'_2(0) - \sigma'_2(1.25 \times \text{FSM\_DOL})) \times 1.25 \times \text{FSM\_DOL}}{T - 1.25 \times \text{FSM\_DOL}} \quad (2)$$

From there, one can (repeating the previous equations) then compute the total center tension equals the sum of the contributions of the spike and of the power-law portion:

$$CT_{tot} = CT_{par} + CT_{spike} \quad (7)$$

If desired the depth of compression of the spiked power-law profile can be calculated/estimated by using the expression:

$$DOCtotal = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx \quad (2)$$

$$DOC_{par}\left(1 - \frac{CT_{sp}}{2CT_{par}(\sqrt{3} - 1)}\right) \approx DOC_{par} - \frac{0.5T}{\sqrt{3}} \frac{CT_{sp}}{2CT_{par}}$$

These equations assume that the deep part of the profile is approximately parabolic in nature and has an added spike near the surface. Its validity is better matched when the spike is small in stress amplitude and not so deep in comparison to the deeper power-law portion of the profile.

Figure 6:
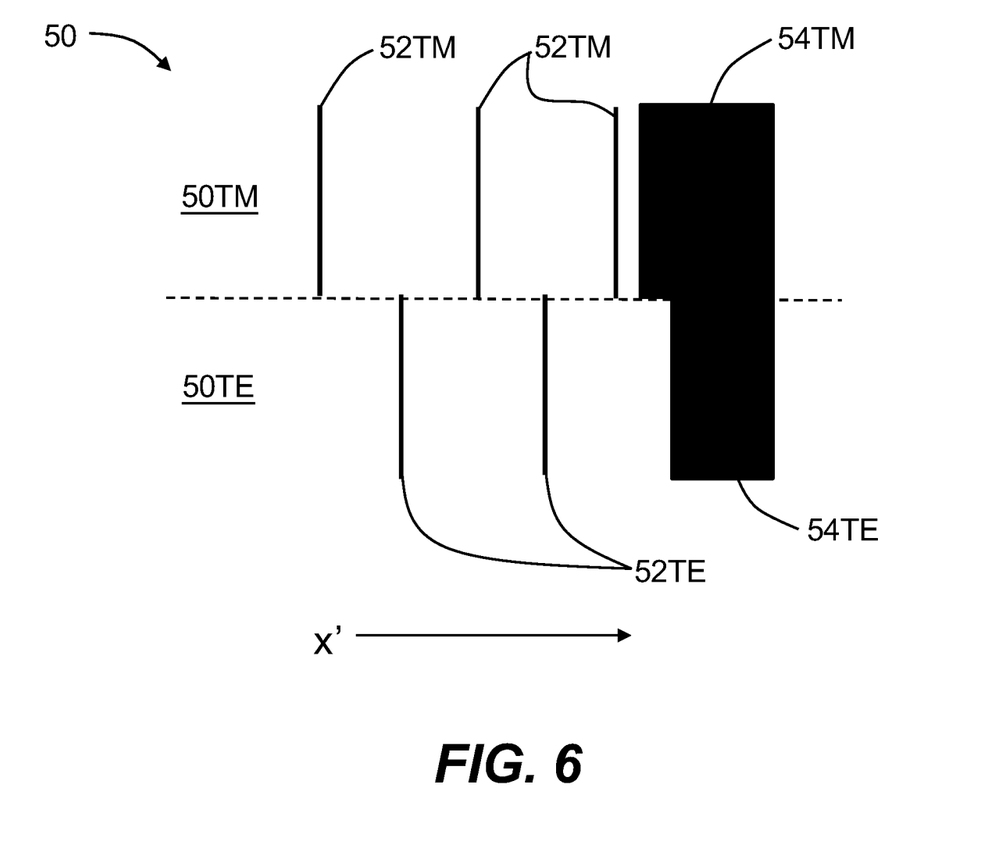
FIG. 6 is a schematic representation of a measured mode spectrum showing the TE and TM mode spectra for an example chemically strengthened Li-containing glass sample.
Figure 7A:
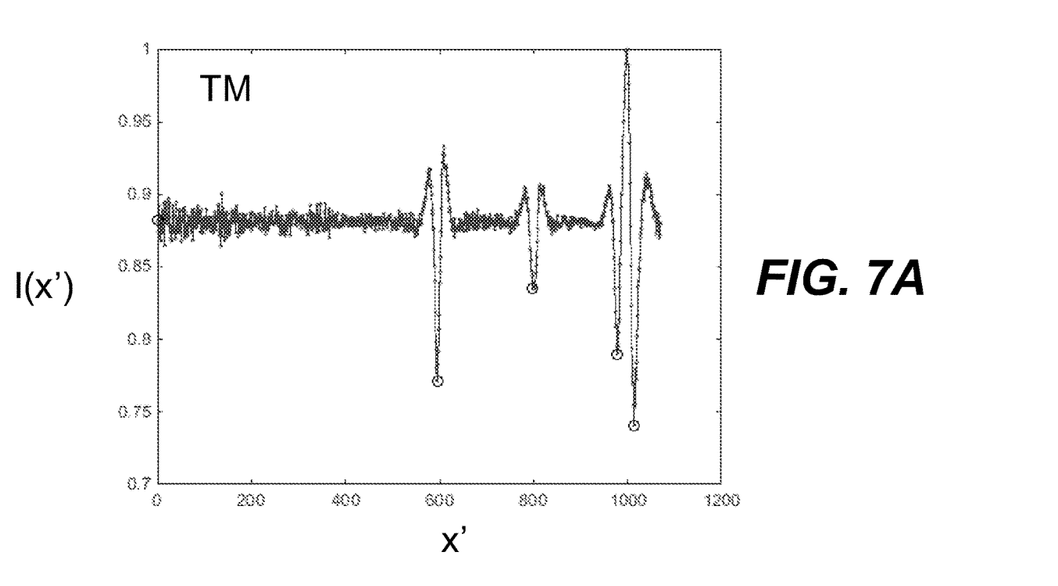
FIGS. 7A and 7B are plots of the intensity I versus distance x' along the mode spectrum for the mode lines or fringes of TE and TM mode spectra, respectively, of FIG. 6.
Figure 7B:
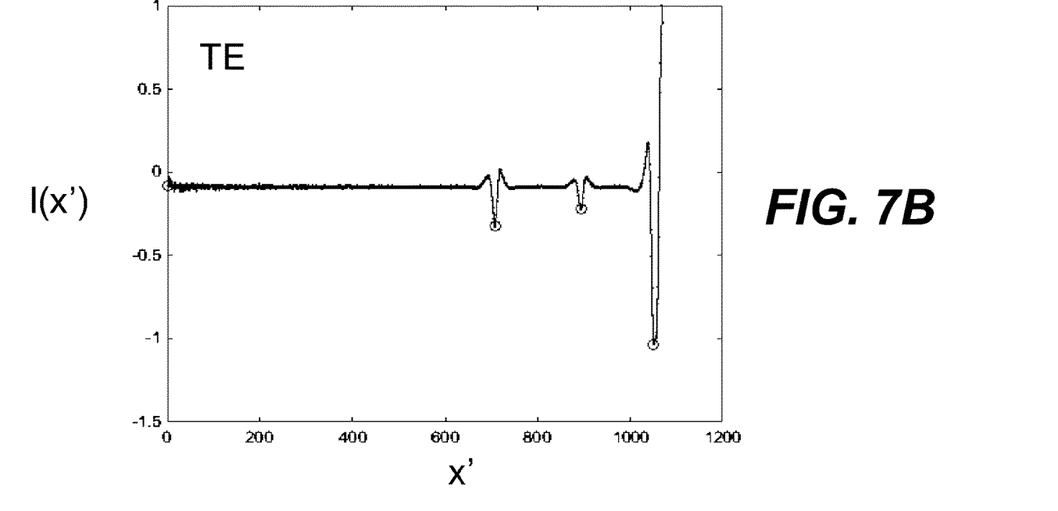

An aspect of the disclosure is the use the algorithm described by the above equations to process measured mode spectra. FIG. 6 is a schematic representation of a measured mode spectrum showing the TE and TM mode spectra based on actual measured mode spectra for an example chemically strengthened Li-containing glass sample. In this case using the algorithm above considering that both $\sigma_2'(125 \times \text{FSM\_DOL}) \sim CS_{knee}$ and that $$\sigma'_1\left(\frac{3 \times \text{FSM\_DOL}}{L}\right) \sim CS_{knee} \quad 65$$

as reasonable approximations, one can find that:

FSM_DOL=$DOL_{sp}$=7.77 um $\sigma_2'(0)=CS_{spike}$=482.6 MPa $CS_{knee}$=138.8 MPa $CT_{spike}$=4.23 MPa $CS_{parabola}=\sigma_1(0)$=172.3 MPa $CT_{parabola}$=86.14 MPa $CT_{total}$=90.4 MPa $DOC_{parabola}$=169 um $DOC_{total}$=163.4 um The method of measurement of the compression at the knee as described above has some accuracy limitations. For any particular measurement wavelength, there are certain quasi-periodic ranges of the spike DOL within which the accuracy of the measurement of the critical-angle shift is reduced. The cause of this reduction is the appearance of a leaky mode with an effective index close to that of the critical angle as the DOL is increased from a range where the critical-angle transition is clear-cut.

In the example of FIG. 3, the signature of such a leaky mode can be observed in the TM mode spectrum as the extra-dark relatively narrow band immediately on the right-hand-side of the transition from bright to dark. When the leaky mode has an effective index very close to the critical-angle index, the shape of the critical-angle transition is changed by the leaky mode, resulting in error in the measurement of the shift. When a leaky mode affects only the critical-angle transition for the TM spectrum, the compression at the knee is slightly over-estimated. When it affects only the critical-angle transition for the TE spectrum, the compression at the knee is slightly under-estimated. When a leaky mode affects both the TM and the TE transition, the net error of the compression at the knee could be positive or negative, and smaller as compared to the error when the transition for only one polarization is substantially affected.

Consequently, aspects of the measurement methods disclosed herein are directed to eliminate or mitigate the error in the measurement of the knee compression that is caused by the presence of a leaky mode. In one embodiment, the target $DOL_{sp}$ is selected such that the effective index of a leaky mode is not close to the critical-angle transition, neither for the TM nor for the TE polarization. If such a choice of $DOL_{sp}$ is not available within the range of preferable overall product stress-profile designs, then the measurement wavelength is chosen such that a leaky mode at the measurement wavelength is not close to the critical angle at either polarization. The way the DOL is measured traditionally is by assigning a fraction of a mode to the index range between the highest-order guided mode and the critical angle for the purposes of mode counting, to provide a continuous measured DOL as a function of increasing diffusion depth by using a continuously varying number of modes.

The equation for the DOL is:

$$DOL = \frac{(2N - 0.5)\lambda}{3.77\sqrt{n\Delta n}}$$

where n is the approximate average index of the measured waveguiding layer, and $\Delta n$ is the difference between the maximum and minimum index of the waveguide assumed to have a truncated linear profile. In the case of the measurement of the spike, $\Delta n$ refers to the difference between the surface index and the index at the knee of the stress profile. N is the continuous number of modes. In the example of FIG. 3, N is approximately 2.6 modes for the TM spectrum and 2.4 modes for the TE spectrum.

The condition for selecting a preferred target DOL or a preferred measurement wavelength is that the non-integer part of the number of modes N be between about 0.1 and 0.6 at both the TM and TE polarization. Hence, in one embodiment of the invention, the measurement wavelength and the depth of the spike are such that the non-integer part of the number of modes is between about 0.1 and 0.6 at both polarizations, preferably between 0.2 and 0.55.

In another less restrictive embodiment, a correction for the effect of the leaky mode is made during the interpretation of the measured shift of the critical transition. The non-integer part of each of the TM and TE number of modes is taken into account, and a correction is made that accounts effect of the leaky mode. To this end, a calibration of the effect of the leaky mode of each polarization on the measured knee compression may be used. In an example, a sequence of samples having $DOL_{sp}$ increasing in small steps is fabricated in the same salt mixture and at the same temperature, and used for the calibration. The actual compression at the knee decreases monotonically and smoothly with increasing $DOL_{sp}$, while the estimated compression fluctuates above and below the smooth dependence of the actual compression on $DOL_{sp}$ as a result of the error induced by the leaky mode. By tracking the dependence of the fluctuation on the non-integer part of the TM and TE mode numbers, the calibration of the necessary correction is obtained.

In another embodiment, the intensity profile in the vicinity of the critical angle is analyzed, the contribution of the leaky mode is estimated based on the shape of the intensity profile and the non-integer mode number, and the estimated contribution is corrected for in the intensity profile to calculate a more accurate position of the critical angle. This is done independently for the TM and the TE polarization, and the stress at the knee is estimated after the TM and TE critical angles are found following the application of the intensity corrections.

In another embodiment, the weight gain of a sample as a result of ion exchange is used in combination with the prism-coupling measurement. The weight gain may be used to verify that enough Na ions have exchanged for Li ions such that the use of the power-law profile model is valid for quality control. For the purpose, a target acceptable weight gain range is prescribed for the ion exchange based on the total surface area of the sample and the sample thickness. The weight of representative samples is measured before and after ion exchange, and the quality-control prism-coupling measurements are considered valid if the measured weight gain per sample falls in the target range.

In another embodiment of the method, advantage is taken of the precise control of the sample shape, and of individual-sample thickness measurements that are common in some production processes. In this case it is possible to verify that the sample has had adequate weight gain by simply measuring the sample thickness with high precision (such as +/−2 microns), and measuring the post-ion exchange weight of the sample. From the known shape specification, the measured thickness, and the known density of the pre-ion-exchanged glass, the weight of the pre-ion-exchanged sample is calculated. A correction factor may be applied that accounts for a typical volume change as a result of ion exchange. The weight gain then is estimated by subtracting from the measured post-ion-exchange weight the estimated pre-exchanged weight. If the weight gain falls within the target range, the profile is deemed adequately represented by the quality-control model profile, and the prism-coupling QC measurement is considered valid.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of improving a functionality of a prism-coupling system having a controller to perform quality control of a chemically strengthened lithium-containing glass sample, the method comprising:
   a) measuring a mode spectrum of the chemically strengthened lithium-containing glass sample using the prism-coupling system;
   b) using the controller, determining a non-integer part of a number of modes of the mode spectrum; and
   c) comparing the non-integer part of the number of modes to a non-integer part of the number of modes specification to determine whether the chemically strengthened lithium-containing glass sample satisfies a quality control specification, wherein the non-integer part of the number of modes specification is from greater than or equal to 0.1 to less than or equal to 0.6.

2. The method of claim 1, wherein the non-integer part of the number of modes specification is from greater than or equal to 0.2 to less than or equal to 0.55.

3. The method of claim 1, wherein the non-integer part of the number of modes is determined for a transverse magnetic (TM) polarization or a transverse electric (TE) polarization.

4. The method of claim 1, wherein the non-integer part of the number of modes for both a transverse magnetic (TM) polarization is compared to the non-integer part of the number of modes specification and a transverse electric (TE) polarization is compared to the non-integer part of the number of modes specification.

5. The method of claim 1, further comprising estimating a depth of compression (DOC) of the chemically strengthened lithium-containing glass sample.

6. The method of claim 5, wherein the estimating the depth of compression (DOC) uses the non-integer part of the number of modes.

7. The method of claim 1, further comprising estimating a central tension of the chemically strengthened lithium-containing glass sample.

8. The method of claim 7, wherein estimating the central tension comprises estimating: i) a spike center tension ($CT_{sp}$) for the spike region only, and ii) a deep region center tension ($CT_{par}$) as produced by the deep region only.

9. The method of claim 8, wherein the deep region center tension ($CT_{par}$) is estimated by assuming a power-law stress profile.

10. The method of claim 9, wherein the power-law stress profile is approximated to be substantially parabolic.

11. The method of claim 8, further comprising comparing a total central tension to a center tension specification, wherein the total central tension is equal to a sum of the spike center tension ($CT_{sp}$) for the spike region only and the deep region center tension ($CT_{par}$).

12. A method of improving a functionality of a prism-coupling system to measure a depth of compression (DOC) in a chemically strengthened lithium-containing glass sample having a surface and a body with a thickness (T), wherein the chemically strengthened lithium-containing glass sample has been strengthened by performing an ion-exchange process that exchanges lithium ions (Li+) in the glass sample with sodium ions (Na+) and potassium ions (K+), the method comprising:
   a) measuring a mode spectrum of the chemically strengthened lithium-containing glass sample using the prism-coupling system; and
   b) estimating the depth of compression (DOC) from the mode spectrum.

13. The method of claim 12, wherein estimating the depth of compression (DOC) from the mode spectrum comprises estimating: i) a spike center tension ($CT_{sp}$) for the spike region only, and ii) a deep region center tension ($CT_{par}$) as produced by the deep region only.

14. The method of claim 13, wherein the deep region center tension ($CT_{par}$) is estimated by assuming a power-law stress profile.

15. The method of claim 14, wherein the power-law stress profile is approximated to be substantially parabolic.

16. The method of claim 13, further comprising comparing a total central tension to a center tension specification, wherein the total central tension is equal to a sum of the spike center tension ($CT_{sp}$) for the spike region only and the deep region center tension ($CT_{par}$).

* * * * *